United States Patent
Picha et al.

(10) Patent No.: US 9,027,929 B2
(45) Date of Patent: May 12, 2015

(54) FLUIDIC PROCESSOR AND METHOD OF USE

(76) Inventors: Neil R. Picha, Petaluma, CA (US);
Bruce D. Black, Napa, CA (US);
Jonathan D. Thompson, Center City, MN (US)

(*) Notice: Subject to any disclaimer, the term of this patent is extended or adjusted under 35 U.S.C. 154(b) by 791 days.

(21) Appl. No.: 13/233,495

(22) Filed: Sep. 15, 2011

(65) Prior Publication Data
US 2012/0086171 A1 Apr. 12, 2012

Related U.S. Application Data

(60) Provisional application No. 61/391,054, filed on Oct. 7, 2010.

(51) Int. Cl.
| | | |
|---|---|---|
| *G01N 1/00* | (2006.01) | |
| *G01N 35/10* | (2006.01) | |
| *B01L 3/00* | (2006.01) | |
| *G01N 30/46* | (2006.01) | |
| *G01N 30/84* | (2006.01) | |
| *G01N 35/00* | (2006.01) | |

(52) U.S. Cl.
CPC .............. *G01N 35/1097* (2013.01); *B01L 3/565* (2013.01); *B01L 3/567* (2013.01); *G01N 30/463* (2013.01); *G01N 30/468* (2013.01); *G01N 2030/8411* (2013.01); *G01N 2035/00277* (2013.01)

(58) Field of Classification Search
CPC ..................................................... F16K 11/074
USPC ....................................... 137/625.46; 422/103
See application file for complete search history.

(56) References Cited

U.S. PATENT DOCUMENTS

| | | | |
|---|---|---|---|
| 3,103,233 A * | 9/1963 | Wulf | 137/625.25 |
| 3,246,667 A | 4/1966 | Pemberton | |
| 4,284,103 A * | 8/1981 | Pemberton | 137/625 |
| 4,531,840 A | 7/1985 | Clark | |
| 4,655,095 A | 4/1987 | Russo et al. | |
| 5,695,720 A | 12/1997 | Wade et al. | |
| 6,257,279 B1 | 7/2001 | Peltz | |
| 6,632,404 B1 | 10/2003 | Freitag et al. | |
| 6,672,336 B2 | 1/2004 | Nichols | |
| 6,748,975 B2 | 6/2004 | Hartshorne et al. | |
| 8,662,099 B2 * | 3/2014 | Arnold et al. | 137/312 |
| 2010/0001220 A1 * | 1/2010 | McLean et al. | 251/314 |
| 2011/0114869 A1 * | 5/2011 | Schaeffer et al. | 251/366 |

FOREIGN PATENT DOCUMENTS

| | | |
|---|---|---|
| WO | WO91/13278 | 9/1991 |
| WO | PCT/SE2009/051276 | 11/2009 |

\* cited by examiner

*Primary Examiner* — Gilbert Lee
(74) *Attorney, Agent, or Firm* — Jerry Haynes Law

(57) ABSTRACT

A fluidic processor includes a first sealing member having a first sealing face, a first compressive face and at least one first sealing member fluid conduit; a second sealing member having a second sealing face, a second compressive face and at least one second sealing member fluid conduit; the second sealing face of the second sealing member being sealingly and slidingly engaged in a substantially fluid tight manner with the first sealing face of the first sealing member; and at least one actuator mechanically engaging at least one of the first sealing member and the second sealing member, or an XY stage, or mechanism that provides motion in two axes on one sealing member only.

20 Claims, 13 Drawing Sheets

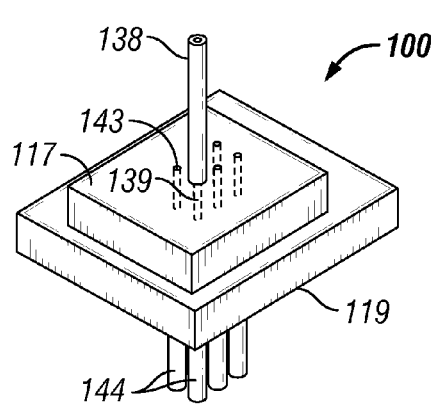
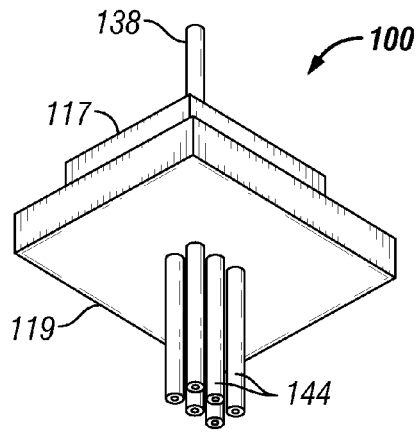
FIG. 4A  FIG. 4B
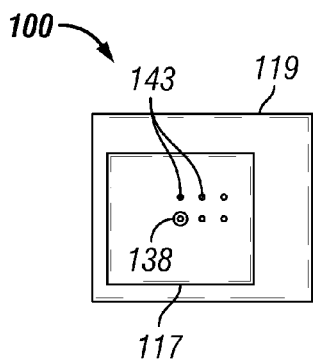
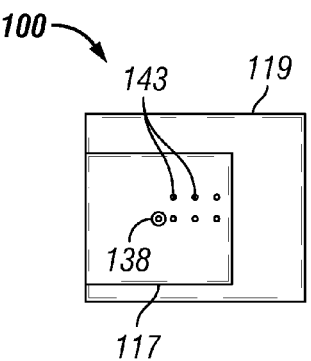
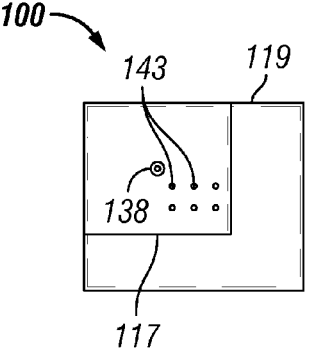
FIG. 4C  FIG. 4D  FIG. 4E
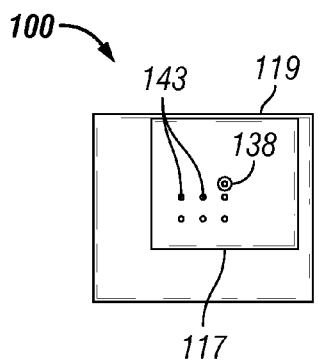
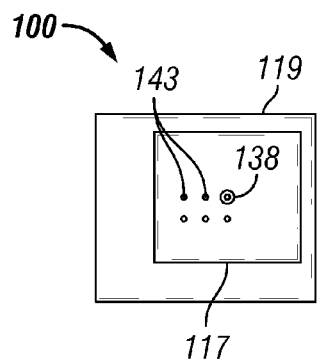
FIG. 4F  FIG. 4G

| STEP (A,B) | SIMPLE OPERATION | RANDOM ACCESS OPERATION | RANDOM ACCESS OF MULTIPLE DEVICES | MASSIVELY PARALLEL REACTION AND DETECTION | Z AXIS SEALING AND REPLACEABLE SEAL |
|---|---|---|---|---|---|
| 1 | SELECT TARGET FLUID COMMUNICATION COORDINATES | SELECT TARGET FLUID COMMUNICATION COORDINATES | SELECT TARGET FLUID COMMUNICATION COORDINATES | SELECT TWO TARGET ARRAY COORDINATES | SELECT TARGET FLUID COMMUNICATION COORDINATES |
| 2 | SELECT CURRENT LOCATION COORDINATES | SELECT CURRENT LOCATION COORDINATES | SELECT CURRENT DEVICES TO BRING ON AND OFF LINE | SELECT OPERATION TYPE | SELECT CURRENT LOCATION COORDINATES |
| 3 | CALCULATE PATH TO CONNECT COORDINATES | CALCULATE PATH TO CONNECT COORDINATES SUBJECT TO SELECTABLE RESTRAINTS | SELECT SEQUENCE TO BRING THEM ON AND OFF LINE CALCULATE PATH TO CONNECT COORDINATES SUBJECT TO SELECTABLE RESTRAINTS | CALCULATE PATH TO CONNECT COORDINATES SUBJECT TO SELECTABLE RESTRAINTS | CALCULATE PATH TO CONNECT COORDINATES SUBJECT TO SELECTABLE RESTRAINTS |
| 4 | SEND PATH PROGRAM TO ACTUATORS | SEND PATH PROGRAM TO ACTUATORS | SEND PATH PROGRAM TO ACTUATORS | SEND PATH PROGRAM TO ACTUATORS | SEND PATH PROGRAM TO ACTUATORS |
| 5 | EXECUTE PROGRAM | EXECUTE PROGRAM | EXECUTE PROGRAM | EXECUTE PROGRAM | EXECUTE PROGRAM |
| 6 | | | | | RELEASE Z ACTUATOR |
| 7 | | | | | ACTUATE AND CYCLE X CADDY |
| 8 | | | | | ALIGN NEW SEAL WITH LOCATION SENSORS |
| 9 | | | | | COMPRESS WITH Z ACTUATOR |

A ALL PROGRAMS VERIFY CURRENT LOCATION PRIOR TO MOVEMENT AND TARGET LOCATION AFTER MOVEMENT WITH POSITION SENSORS.
B USER SELECTABLE RESTRAINTS INCLUDE BUT ARE NOT LIMITED TO RANDOM ACCESS AND RANDOM ACCESS WITH NO CROSS TALK.

*FIG. 10*

FLUIDIC PROCESSOR AND METHOD OF USE

CROSS-REFERENCE TO RELATED APPLICATIONS

This application claims the benefit of U.S. provisional application No. 61/391,054, filed Oct. 7, 2010 and entitled "Fluidic Processor", which provisional application is incorporated by reference herein in its entirety.

BACKGROUND OF THE INVENTION

Fluidic systems are currently used in many industries. Devices that incorporate fluidic systems include but are not limited to DNA analyzers, clinical chemistry analyzers, high pressure liquid chromatography analyzers, lab-on-a-chip devices, and a myriad of micro and macro fluidics sample handling and preparation systems. These fluidic systems typically rely on discrete fluidic components such as tubings, fittings, pumps, valves and precision dispensing equipment to treat, modify, inject and otherwise manipulate analytes and diluents for the purposes of treating, reacting, detecting or quantifying the analyte in solution. Currently available fluidics systems are designed to make and break fluidic connections in a sequential, adjacent discrete fashion. Therefore, conventional fluidic systems operate like a scroll or a cassette tape, moving fluids sequentially with no provision to randomly access discontiguous fluid conduits without first encountering adjacent fluid conduits. This drawback greatly limits the complexity of operations that may be completed with a single device or combinations of components.

Other key disadvantages of conventional fluidic designs include carry-over of analyte from one discrete channel to another upon switching fluidic paths. For example, consider a fluidic stream selector rotary valve that is commonly known in the art with three positions A, B and C that connect the three distinct fluid paths A, B and C to a common outlet Z. When the valve is in position A, fluid A is in fluid communication with outlet Z. Likewise, when the valve is in position B, fluid B is in fluid communication with outlet Z. During an actuation event in which position A is switched to position C, the device must traverse position B, potentially contaminating fluid B with fluid A. This problem is inherent in the sequential operation of the rotary design and is commonly termed "sample carry over" in the art.

Another example of a similar drawback which characterizes conventional fluidic designs can be illustrated with a conventional rotary injection valve that has two positions A and B. In this case, position A is at low fluidic pressure and incorporates a fluidic conduit A that is loaded with analyte A. Position B is at high fluidic pressure and incorporates a fluidic conduit B. When the valve switches from position A to position B, the analyte A in the fluid conduit a empties into the fluid conduit B, thereby allowing the analyte to be loaded into conduit A at low pressure and injected into conduit B at high pressure. The problem with this device is that analyte A can adsorb or stick to fluid conduit A and not fully empty into fluid conduit B. This causes carry over and an error in the measured amount of analyte A in an injected sample. Another disadvantage of conventional fluidic design devices includes cross talk, which occurs when fluid leaks between various positions in a valve (as in the example above, in which fluid A leaks into fluid B).

There are manifolds currently available on the market that integrate fluidic components and connections and are found in many clinical analyzers. However, these fluidic systems are not characterized by a random access operating sequence and cannot provide dynamic interchangeable fluidic seals and configurable elements.

SUMMARY OF THE INVENTION

The disclosure is generally directed to a fluidic processor which can be operated according to a random access operating sequence. An illustrative embodiment of the fluidic processor includes a first sealing member having a first sealing face, a first compressive face and at least one first sealing member fluid conduit; a second sealing member having a second sealing face, a second compressive face and at least one second sealing member fluid conduit; the second sealing face of the second sealing member being sealingly and slidingly engaged in a substantially fluid tight manner with the first sealing face of the first sealing member; and at least one actuator mechanically engaging at least one of the first sealing member and the second sealing member.

BRIEF DESCRIPTION OF THE DRAWINGS

The disclosure will now be made, by way of example, with reference to the accompanying drawings, in which:

FIG. 4A is a top perspective view of a simplified illustrative embodiment of the fluidic processor in exemplary application of the fluidic processor;

FIG. 4B is a bottom perspective view of the illustrative embodiment of the fluidic processor illustrated in FIG. 4A;

FIGS. 4C-4G illustrate sequential steps carried out in random access operation of the fluidic processor;

FIG. 10 is a flow chart showing a method embodiment for various random access processes in implementation of the fluidic processor;

DETAILED DESCRIPTION

The following detailed description is merely exemplary in nature and is not intended to limit the described embodiments or the application and uses of the described embodiments. Other embodiments are recognized as being within the grasp of those having ordinary skill in the art. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary or the following detailed description. As used herein, relative terms such as "upper" and "lower" are intended to be used in an illustrative and not a limiting sense. In some applications, therefore, those elements which are identified as "upper" may be located beneath those elements which are identified as "lower" in the following detailed description. Relative terms such as "top", "bottom", "upper", "lower" and "side" as used herein are to be construed as descriptive for purposes of understanding operation of the dispensing and sealing assembly as it is used in some exemplary applications and such relative terms may not apply in other applications. Therefore, such relative terms are not to be construed as limiting the scope of the appended claims.

With respect to the present disclosure, a "fluid" includes any gas or liquid. "Make and break" is the process by which fluidic conduits are moved from a fluidic address located at a first location specified by a first set of Cartesian coordinates at which fluid communication is already established to a desired fluidic address at a second location specified by a second set of Cartesian coordinates whereby fluid communication is discontinued at the first location and reestablished at the second location. "Random access" is the process by which an arbitrary fluidic element in an array of fluidic elements is accessed without traversing any other fluidic element.

Figure 1:
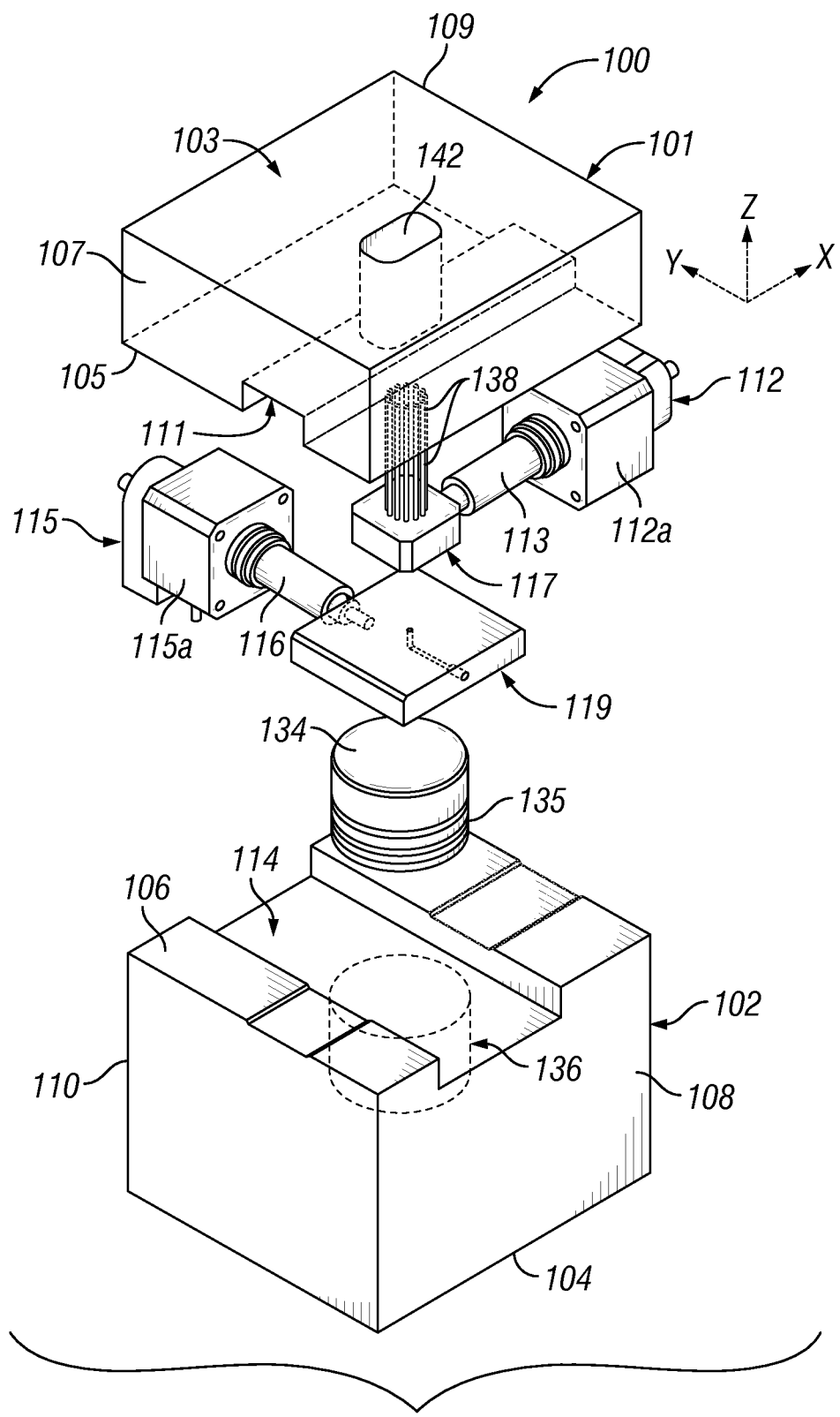
FIG. 1 is an exploded perspective view of an illustrative embodiment of the fluidic processor.
Figure 2:
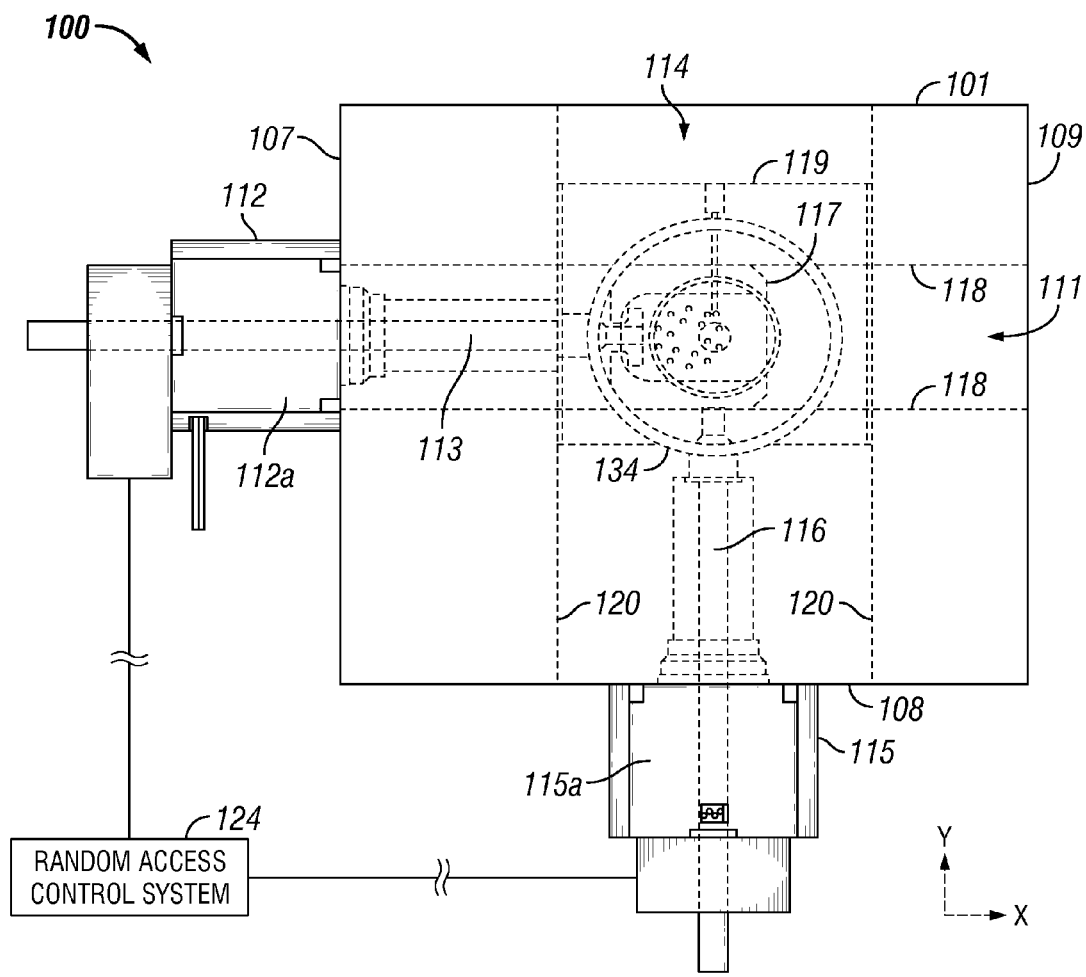
FIG. 2 is a top view of an illustrative embodiment of the fluidic processor.
Figure 3:
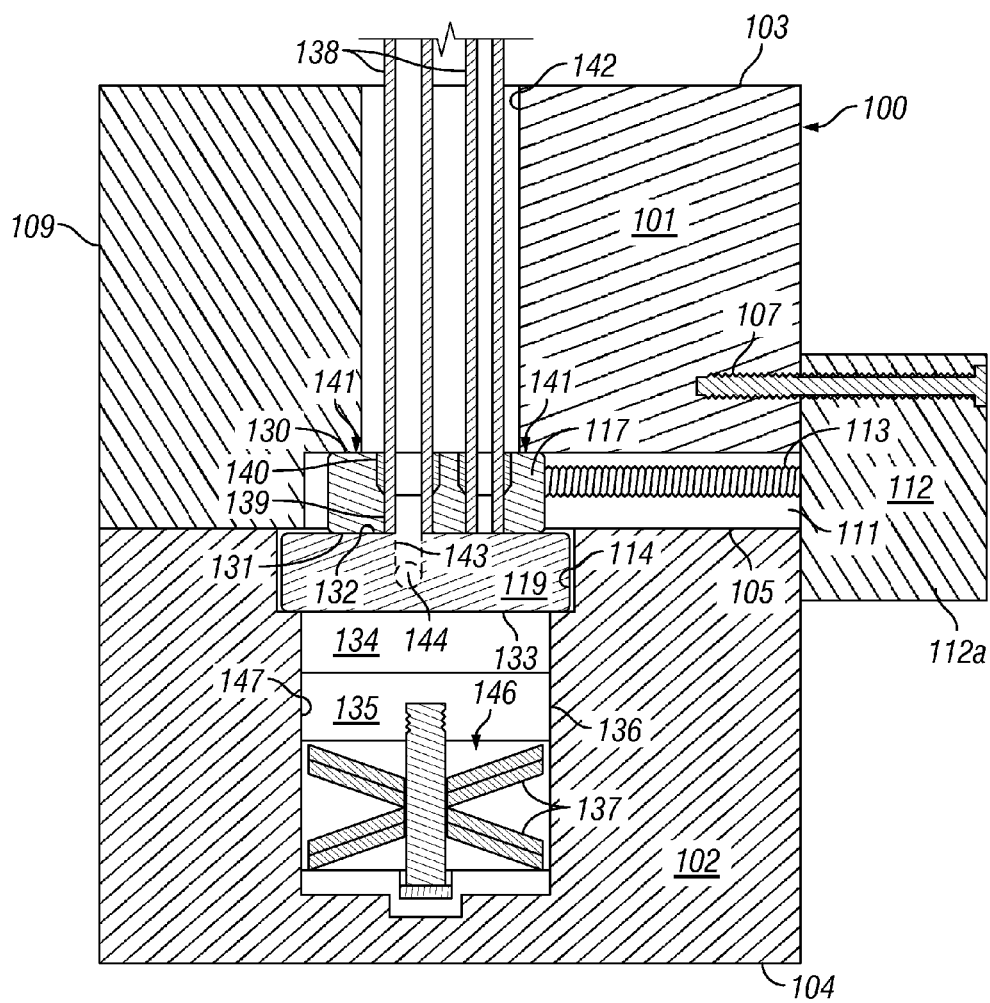
FIG. 3 is a cross-sectional view of an illustrative embodiment of the fluidic processor.

Referring initially to FIGS. 1-3 of the drawings, an illustrative embodiment of the fluidic processor of the present disclosure is generally indicated by reference numeral 100. The fluidic processor 100 may include a first housing 101. The first housing 101 may include a first housing external face 103, a first housing internal face 105 which is opposite the first housing external face 103, a first housing first side 107 and a first housing second side 109 which is opposite the first housing first side 107. A first channel 111 having first channel walls 118 (FIG. 2) may be provided in the first housing internal face 105. The first channel 111 may extend from the first housing first side 107 to the first housing second side 109. As illustrated in FIG. 2, a first linear actuator 112 may include a first linear actuator housing 112a and a first linear actuator shaft 113 which is selectively extendable from and retractable into the first linear actuator housing 112a. The first linear actuator housing 112a of the first linear actuator 112 may be provided at the first housing first side 107 of the first housing 101. The first linear actuator shaft 113 may be selectively extendable from the first linear actuator housing 112a coaxially into the first channel 111. For purposes of description and not limitation, in some applications of the fluidic processor 100, the first channel 111 and the first linear actuator shaft 113 of the first linear actuator 112 may be substantially aligned with the X axis of a Cartesian coordinate system, as shown in FIGS. 1 and 2.

The fluidic processor 100 may further include a second housing 102 which is generally adjacent to the first housing 101. The second housing 102 may include a second housing external face 104, a second housing internal face 106 which is opposite the second housing external face 104, a second housing first side 108 and a second housing second side 110 which is opposite the second housing first side 108. As illustrated in FIG. 1, the second housing internal face 106 of the second housing 102 may face the first housing internal face 105 of the first housing 101. A second channel 114 having second channel walls 120 (FIG. 2) may be provided in the second housing internal face 106. The second channel 114 may extend from the second housing first side 108 to the second housing second side 110.

As further illustrated in FIG. 2, a second linear actuator 115 may include second linear actuator housing 115a and a second linear actuator shaft 116 which is selectively extendable from and retractable into the second linear actuator housing 115a. The second linear actuator housing 115a of the second linear actuator 115 may be provided at the second housing first side 108 of the second housing 102. The second linear actuator shaft 116 may be selectively extendable from the second linear actuator housing 115a coaxially into the second channel 114. For purposes of description and not limitation, in some applications of the fluidic processor 100, the second channel 114 and the second linear actuator shaft 116 of the second linear actuator 115 may be substantially aligned with the Y axis of the Cartesian coordinate system, as shown in FIGS. 1 and 2.

A random access control system 124 may interface with the first linear actuator 112 and the second linear actuator 115. The random access control system 124 may be adapted to operate the first linear actuator 112 and the second linear actuator 115 according to a random access control sequence as will be hereinafter described.

As further illustrated in FIGS. 1 and 3, a first sealing member 117 may be disposed for axial displacement in the first channel 111 of the first housing 101. The first linear actuator shaft 113 of the first linear actuator 112 may operably engage the first sealing member 117 to facilitate axial movement of the first sealing member 117 in the first channel 111. Accordingly, the first sealing member 117 may be precision fit to slidably engage the first housing channel walls 118 (FIG. 2) of the first channel 111 in such a manner that the first sealing member 117 traverses the first channel 111 in a linear motion without binding while at the same time minimizing any radial twisting upon linear actuation of the first linear actuator 112. In like manner, a second sealing member 119 may be disposed for axial displacement in the second channel 114 of the second housing 102. The second linear actuator shaft 116 of the second linear actuator 115 may operably engage the second sealing member 119. The first sealing member 117 may extend beyond the first housing internal face 105 of the first housing 101 such that the first sealing member 117 can compressibly engage the second sealing member 119 in the second channel 114 of the second housing 102.

Figure 1A:
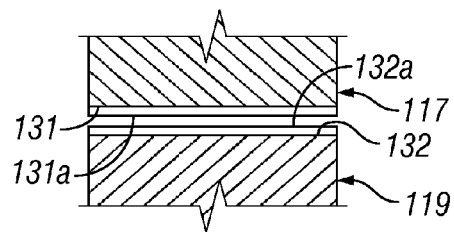
FIG. 1A is a cross-sectional view illustrating a hard lubricious coating on each of the first sealing member and the second sealing member of an illustrative embodiment of the fluidic processor.

As illustrated in FIG. 3, the first sealing member 117 may have a first compressive face 130 and a first sealing face 131 which is opposite the first compressive face 130. The second sealing member 119 may have a second compressive face 133 and a second sealing face 132 which is opposite the second compressive face 133. As illustrated in FIG. 1A, in some embodiments, a hard lubricious coating 131a may be provided on the first sealing face 131 of the first sealing member 117. A hard lubricious coating 132a may be provided on the second sealing face 132 of the second sealing member 119. In the embodiment shown in the FIG. 3, at least one inlet tube 138 may extend through a tube bore 142 in the first housing 103. Each inlet tube 138 may include PEEK, PTFE, FEP and/or any other thermal plastic with sufficient resiliency to maintain a friction fit when exposed to various plasticizing chemicals, large temperature variations or the like.

Each inlet tube 138 may be substantially fluidly sealed and inserted through a corresponding through bore 139 that extends from the compressive face 130 to the sealing face 131 of the first sealing member 117. In some embodiments, a counter bore 140 may extend from the sealing face 130 partially into the first sealing member 117 to prevent skiving of each inlet tube 138 when installed in the through bore 139. Each inlet tube 138 may be unitary and compressively friction fit within the through bore 139 while not being friction fit in the counter bore 140. Friction fit of the inlet tube 138 in the through bore 139 may be reinforced through the use of adhesives, spot welds and the like. The connection can also be made using standard fittings and port details, know to those skilled in the art of fluidic systems, including, but not limited to, interference fits, manifolds, and slipfits. Slipfits are stainless steel tubes pressed in to manifolds, or seals whereby the tubing is pushed over the tube, creating a leak free connection. The inlet tube 138 may be disposed in fluid communication with multiple fluid conduits 143 (one of which is illustrated in phantom in FIG. 3) in the second sealing member 119. At least one external fluid connection 144 may be disposed in fluid communication with each fluid conduit 143. In some embodiments, each external fluid connection 144 may be oriented generally parallel to the plane of the second sealing member 119, as illustrated. In other embodiments, each external fluid connection 144 may extend perpendicularly from the plane of the second sealing member 119, as will be hereinafter described with respect to FIGS. 4A and 4B.

As further illustrated in FIG. 3, a compressive force mechanism 146 may provide uniform compressive force to accomplish sealing between the first sealing face 131 of the first sealing member 117 and the second sealing face 132 of the second sealing member 119. In some embodiments, a compressive force mechanism cavity 147 may be provided in the second housing 102. The compressive force mechanism 146 may be provided in the compressive force mechanism cavity 147 and includes a pre-loaded belleville washer stack 137 that may be pre-compressed with a loading shaft 135 and additional pressure disks 134 which engage the second compressive face 133 of the second sealing member 119 and bias the second sealing member 119 against the first sealing member 117. Accordingly, the belleville washer stack 137 provides the required sealing force to effect a seal between the first sealing member 117 and the second sealing member 119. The loading shaft 135 and the pressure disc 134 may be placed in a z-axis shaft 136 which is located in z-axis alignment with the first sealing member 117 and the sealing member 119. As shown in FIG. 3, upon actuation of the compressive force mechanism 146, the pressure disks 134 may press the second sealing member 119 against the first sealing member 117. The first compression face 130 of the first sealing member 117 may be pressed against a shoulder 141 in the first channel 111 of the first housing 101 to create a fluid-tight seal at the interface between the first sealing face 131 of the first sealing member 117 and the second sealing face 132 of the second sealing member 119.

The materials of construction for the first sealing member 117 and the second sealing member 119 may be selected so as to provide both lubricity and rigidity. Rigidity may be important for the purposes of minimizing upward z axis deflection of the first sealing member 117 and the second sealing member 119 upon compression by operation of the compressive force mechanism 146. Suitable rigid materials for use as the first sealing member 117 and the second sealing member 119 include stainless steel, titanium, PEEK, ceramic, vespel, PPS and other suitable polymers with similar properties. Composites and combinations of polymers with carbon, glass or per fluoropolymer fillings to provide lubricity and strength may also be suitable materials. Z-axis deflection may be minimized by using a rigid metal and a lubricious coating (not illustrated) on the metal such as a carbon or thermally cured fluoropolymer coating, for example and without limitation. Stainless gaskets (not illustrated) with resilient coatings or solid PTFE gaskets may be alternatively used to provide lubricity and sealing quality between friction interfaces. Minimization of friction on all surfaces in contact with sealing members 117, 119 may be desirable. In some embodiments, sealing surfaces may be coated with TEFLON® (polytetrafluoroethylene) or carbon via vapor or plasma deposition. Alternatively, carbon based paste lubricants or self lubricating adhesives may be used to minimize friction on the surfaces.

It may be desirable to minimize lash from screw and motor of the first linear actuator 112 and the second linear actuator 115 and the respective actuator shafts 113, 116 and from interface between the linear actuator shafts 113, 116 and the respective sealing members 117, 119 by judicious selection of linear actuators 112, 115. Low lash linear actuators are commonly available commercially. In some embodiments, lash can be further reduced through the use of one or more preloaded bearings (not illustrated) placed on the linear actuator shafts 113, 116 to provide a constant load upon the linear actuators 112, 115. Alternatively, either or both of the sealing members 117, 119 can be spring-loaded to provide a constant force on the respective linear actuators 112, 115.

Referring next to FIGS. 4A-4G of the drawings, exemplary application of the fluid processor 100 to randomly make and break fluid connections according to a random access operating sequence is illustrated. In the perspective views of FIGS. 4A and 4B, the first sealing member 117 may be generally square-shaped and sealingly engaged with a larger square-shaped second sealing member 119 as detailed above with respect to FIGS. 1-3. In this case, the second sealing member 119 may be fixed and not actuated by the second linear actuator 115 (FIGS. 1-3). The first sealing member 117 may be actuated along both the x and y axes via the first linear actuator 112 in a manner which is similar to the fluidic processor 100 in FIGS. 1-3. The first sealing member 117 may have disposed within it a single through bore 139 with a single inlet tube 138 that may be friction-fit installed in the through bore 139 as was described above with respect to FIGS. 1-3. The second sealing member 119 may include six fluid conduits 143 with six external fluid connections 144 disposed in fluid communication with the respective fluid conduits 143. For purposes of illustration herein, in FIGS. 4C-4G, the fluid conduits 143 in the second sealing member 119 are designated as positions 1-6, respectively.

The random access control system 124 (FIG. 2) is operated to make and break fluid connections according to a random access operating sequence. As illustrated in FIG. 4C, a fluid connection is initially established between the inlet tube 138 and the fluid conduit 143 at position 1. Next, the desired position 2-6 for subsequent establishment of a fluid connection between the inlet tube 138 and the fluid conduit 143 is chosen. For purposes of description herein, it is desirable to establish a fluid connection between the inlet tube 138 and the fluid conduit 143 at position 6. Accordingly, the first sealing member 117 is sequentially moved along the path which is illustrated in FIGS. 4C-4G to establish the fluid connection between the inlet tube 138 and the fluid conduit 143 at position 6. It will be appreciated by those skilled in the art that the inlet tube 138 need not be serially positioned in fluid communication with the fluid conduits 143 at the positions 2-5, respectively, in transit of the inlet tube 138 from the fluid conduit 143 at position 1 to the fluid conduit 143 at position 6.

In some applications, the sequential scroll style fluidics which was heretofore illustrated with respect to FIGS. 4C-4G may be the desired approach to making and breaking fluid connections between the inlet tube 138 and the fluid conduit 143 at the desired position. However, if random fluid connections are desirable, the fluidic processor 100 may be programmed to conform to user-defined constraints. Constraints can be programmed so that no fluid connection is made except the one which is desired. Other embodiments of the fluidic processor 100 may include programs for massively parallel operations or for parking analytes and randomly accessing those analytes based on results from detection feedback. In such applications, the fluidic processor 100 can be operated to access position 6 without traversing positions 2-5 such as in the manner which is illustrated in FIGS. 4C-4G. From the first frame (FIG. 4C) to the second frame (FIG. 4D), the first sealing member 117 moves in the –X direction. Then, from the second frame to the third frame (FIG. 4E), the first sealing member 117 moves in the Y direction so as to avoid connection with any of the other fluid conduits 143 at positions 2-5. From the third frame to the fourth frame (FIG. 4F), the first sealing member 117 moves in the X direction adjacent to the fluid conduit 143 at position 6. In the final step, the first sealing member 117 moves in the –Y direction and the fluid connection between the inlet tube 138 and the fluid conduit 143 at position 6 is established.

It will be appreciated by those skilled in the art that the sealing members 117, 119 of the fluidic processor 100 includes but is not limited to the concept of a static stator/sealing member combination that is machined with grooves in the seal and ports in the stator for a specific function only. The sealing members 117, 119 can also be configured to contain any number of internal fluid conduits 143 (FIG. 3). The internal fluid conduits 143 may be fabricated from layers of bonded polymer or stainless steel having channels that are machined or etched in the surfaces to create multiple fluid conduits 143 intended for a variety of fluidic operations. As shown in FIG. 3, the second sealing member 119 may have an internal fluid conduit 143 and an external fluid connection or port 144 which extends from the second sealing member 119 parallel to the plane of the second sealing member 119. In some embodiments, the sealing members 117, 119 may include multiple internal fluid conduits 143 and external fluid connections or ports 144, as illustrated in FIGS. 4A and 4B. As further illustrated in FIGS. 4A and 4B, the external fluid connections or ports 144 may extend perpendicular to the plane of the second sealing member 119. Additionally, the sealing members 117 and 119 may include multiple positioning sensors (not illustrated) that facilitate alignment of the seal with known locations on both sealing members 117, 119 so that the fluid conduits 143 are registered and when actuated, in fluid communication. Those positioning sensors can be placed in any number of locations in the first housing 101, the second housing 102 or the sealing member 117, 119 itself and can be electrical, optical or physical in nature. The present disclosure anticipates any number of sealing members 117, 119 which may be disposed in fixed or movable relationship with respect to either or both of the first housing 101, the second housing 102 and with each other. Moreover, the first sealing member 117 and the second sealing member 119 may be independently controlled in x, y, z and rotational axes according to the knowledge of those skilled in the art.

As further illustrated in FIG. 2, in some embodiments, the fluidic processor 100 may incorporate multiple inlet tubes 138 and external fluid connections 144 (FIGS. 4A and 4B) that can be configured to provide the needed fluid operation. Likewise, the sealing members 117, 119 can include any number of surface grooves (not illustrated) or fluid conduits (not illustrated) to provide fluidic flexibility. The surface conduits, like the inlet tubes 138 and the internal fluid conduits 143, can be readily incorporated into the fluidic processor 100 for various functions such as to being external devices on line or off line in a random access manner.

Figure 5:
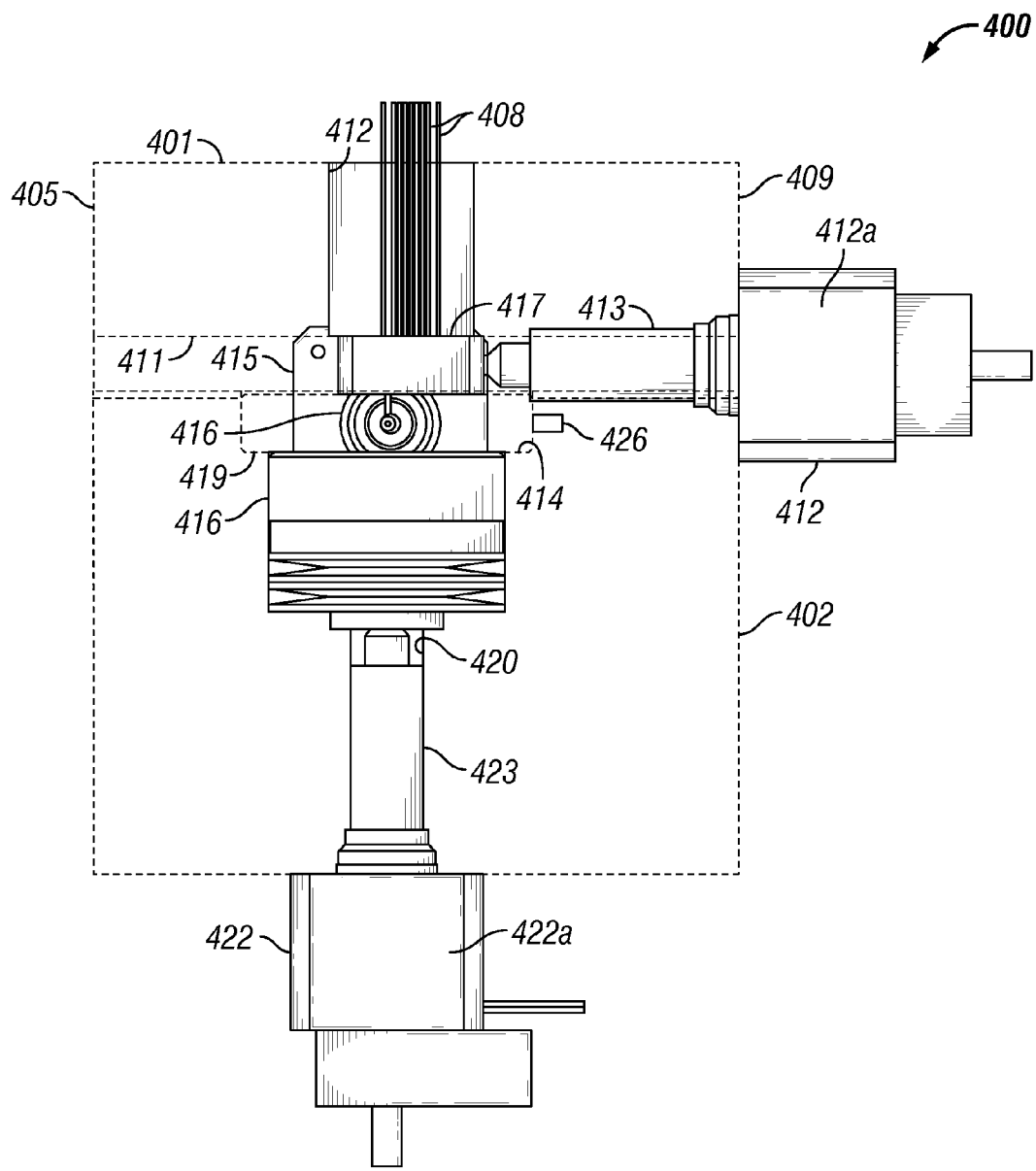
FIG. 5 is an alternative illustrative embodiment of the fluidic processor which incorporates dynamic Z-axis sealing.

Referring next to FIG. 5 of the drawings, a cross sectional view of an alternative illustrative embodiment of the fluidic processor 400 is illustrated. The fluidic processor 400 may be similar in design to the fluidic processor 100 which was heretofore described with respect to FIGS. 1-3, with like numerals in the 400 series of the fluidic processor 400 designating corresponding components indicated by like numerals in the 100 series of the fluidic processor 100. The second housing 402 of the fluidic processor 400 may include a z axis channel 420 that extends along the z-axis (FIG. 1) and accommodates a z axis actuator 422. The z axis actuator 422 may include a z axis actuator shaft 423 which is disposed in operable communication with the pre-loaded compressive force mechanism 416. In some embodiments, the z axis actuator 422 may be a rotary actuator. In other embodiments, the z axis actuator 422 may be a linear actuator. In embodiments in which the z axis actuator 422 is a rotary actuator, all of the necessary encoders and stops that are commonly known in the art may be utilized to effectively control the rotary position of the z axis actuator 422. In conjunction with the first linear actuator 412 (which actuates the first sealing member 417 along the X axis) and the second linear actuator 415 (which actuates the second sealing member 419 along the Y axis), as was heretofore described with respect to the fluidic processor 100, various curvilinear actuation paths can be programmed into the fluidic processor 400. In embodiments in which the z axis actuator 422 is linear, the fluidic processor 400 may be used to dynamically seal the sealing members 417, 419 as needed. For instance, in concert with various leak sensors 426 embedded in second housing 402, the compression force could be controlled to exact an increasing force on the sealing members 417, 419 when a leak is detected. Alternatively, the linear z axis actuator 422 can be used to lessen the z axis compressive force to zero. In this case, fresh sealing members 417, 419 can easily be replaced or dynamically replaced as deemed necessary.

Figure 6:
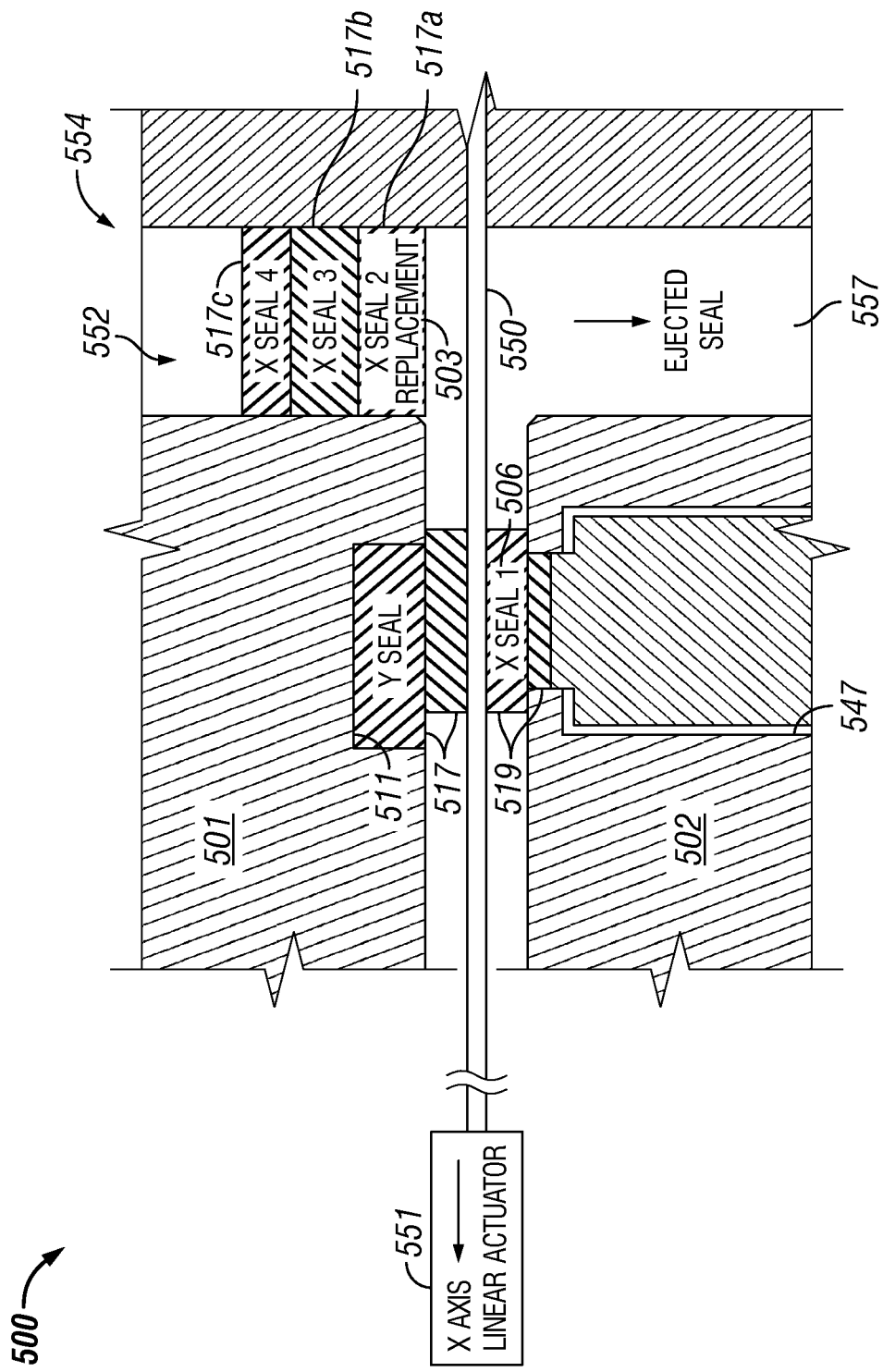
FIG. 6 is a cross-sectional view of an alternative illustrative embodiment of the fluidic processor with sealing member replacement capability.

Referring next to FIG. 6 of the drawings, a cross-sectional view of an alternative illustrative embodiment of the fluidic processor 500 is illustrated. The fluidic processor 500 may be similar in design to the fluidic processor 100 which was heretofore described with respect to FIGS. 1-3, with like numerals in the 500 series of the fluidic processor 500 designating corresponding components indicated by like numerals in the 100 series of the fluidic processor 100. The fluidic processor 500 is amenable to dynamic sealing and dynamic replacement of the first sealing member 517 and the second sealing member 519. The fluidic processor 500 may include a sealing member shuttle 550 that is operably engaged by an X axis actuator 551. The sealing member shuttle 550 may include a seal feed device 554 that provides sealing member replacements 517a-517c to the sealing member shuttle 550 when the X-axis actuator 551 is fully extended to the sealing member shuttle 550. The sealing member replacements 517a-517c can be advanced into the sealing member shuttle 550 from a loading channel 552 with any number of actuators (not illustrated) as is commonly known in the art. In some embodiments, the sealing member replacements 517a-517c may be gravity fed from the loading channel 552 into the sealing member shuttle 550.

The used sealing member 517 which is to be discarded may be simultaneously ejected from between the first housing 501 and the second housing 502 (as illustrated) into an eject channel 557. The load channel 552 and the eject channel 557 can be placed in any location along the x axis including but not limited to disposed within the first housing 501 and/or the second housing 502 and does not necessarily need to be incorporated into the seal feed device 554. In some embodiments, the sealing member shuttle 550 may be omitted and location sensors (not illustrated) and dynamic magnetic attachment of the X-axis actuator 551 to the sealing member 517 may be used to load and position a fresh sealing member 517a-517c in place in the first channel 511. Ejection of the used sealing member 517 can be accomplished with an additional Y-axis actuator (not illustrated) that is in orthogonal relationship to the loading X-axis actuator 551. In this case, the X-axis actuator 551 loads the new seal 517a-517c and the Y-axis actuator ejects the used seal 517. In each of these embodiments, a Z-axis actuator 422 (FIG. 5) may be used to provide compressive force to the sealing members 117, 119 to create a fluidic seal.

In some embodiments (not illustrated), a continuous roll of sealing material may be fed into the fluidic processor 500 on one side and discarded on the opposite side. The sealing members 117, 119 may be registered within the first channel 511 in the first housing 501 using any number of optical, barcode or physical alignment mechanisms known by those skilled in the art. The disposable seals 517 may be continuous or discrete. In some embodiments, the disposable seals 517 may be electrochemical flow strips such as lateral flow strips commonly known in the art. In this case, the fluidic processor 500 may be used to spot an analyte onto the dynamic seal and an electrochemical signal would be read directly from the seal. Alternatively, compression members (not illustrated) can be incorporated directly into the sealing members 517, 519, thereby eliminating the need for any z axis compression. This may be accomplished by incorporating machined keyways (not illustrated) into the sealing members 517, 519.

Figure 7:
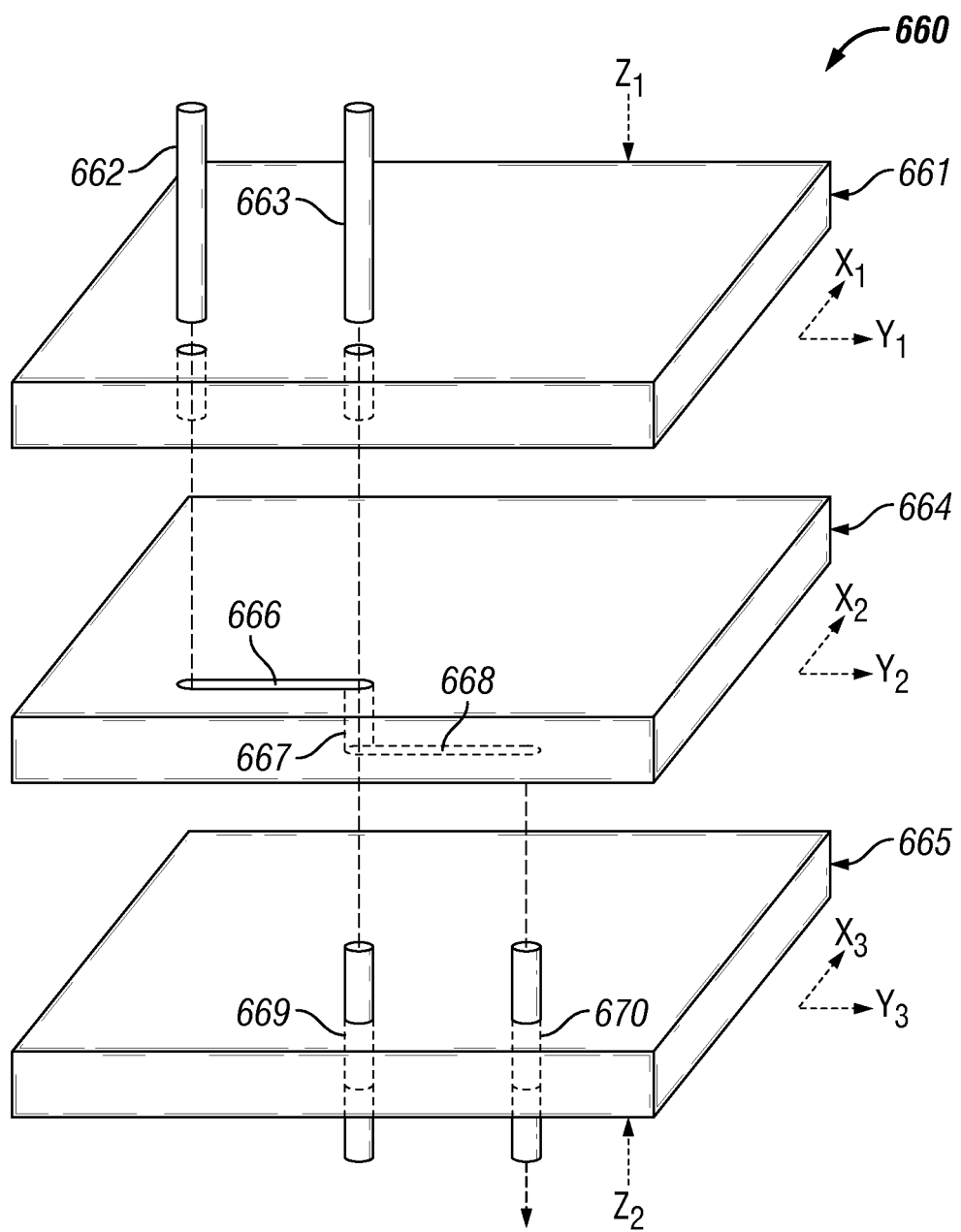
FIG. 7 is an exploded perspective view of an exemplary seal assembly which is suitable for implementation of an illustrative embodiment of the fluidic processor.

Referring next to FIG. 7 of the drawings, a perspective view of a seal assembly which is suitable for implementation of an illustrative embodiment of the fluidic processor 100 is generally indicated by reference numeral 660. The seal assembly 660 may include a first seal 661 having at least one fluid inlet conduit 662. At least one optical fiber 663 may extend through the first seal 661. The optical fiber 663 may be any type of optical fiber having any type of cladding that transmits any wavelength of light as is commonly known by those skilled in the art. The optical fiber 663 may be compressively attached to the first seal 661 in a similar fashion as the fluid inlet conduit 662. However, in some applications, a complaint polymeric sleeve (not illustrated) may be necessary to provide the necessary resilience and compression between the optical fiber 663 and the first seal 661. In some embodiments, the optical fiber 663 may be replaced with an electrode (not illustrated). In the case of an ion selective electrode such as a pH electrode, an external reference electrode (not illustrated) may also need to be incorporated into the same fluidic path to complete the circuit.

Not only can the optical fiber be used to detect analytes or reactions, but optical fibers and LED's can be incorporated into the seal, or linear actuator, or stage to provide absolute position feedback. Since discrete positions will determine the fluidic connections to be made, there may be only two to ten discrete positions. Since the final destination is what is really of interest, intermediate positions are not important.

A second seal 664 may be sandwiched between the first seal 661 and a third seal 665. The second seal 664 may include any number of surface conduits 666 and 668 which may be connected to each other through bores 667, internal conduits (not shown), or external ports (not shown). In this case, each bore 667 may incorporate a liquid core waveguide material (not illustrated) such as Teflon® AF. Accordingly, a small bore waveguide (not illustrated) may be compressibly installed in the second seal 664 using a compliant resilient sleeve (not illustrated). In order to reduce optical noise from scattering, the optical fiber 663 can be sized to match the inside diameter of the waveguide and dynamically located with the x, y actuation mechanism. The second seal 664 may be a replaceable seal whereas the third seal 665 and the first seal 661 may be fixed in relation to the second seal 664. It will be appreciated by those skilled in the art that the seal assembly 660 may be incorporated into the design of the fluidic processor 500 which was heretofore described with respect to FIG. 6. The third seal 665 of the seal assembly 660 may include at least one optical exit fiber 669 and at least one fluid exit conduit 670. The optical exit fiber 669 may be an optical window or an optical fiber.

In operation of the fluid processor 100, fluid and analyte (not illustrated) enters the seal assembly 660 through the fluid inlet conduit 662 and traverses surface conduit 666 of the second seal 664. The analyte is detected in the bore 667 and exits the bore 667 through the surface conduit 668. From the surface conduit 668, the analyte enters the fluid exit conduit 670. The radiant energy which is emitted from the optical fiber 663 interacts with the analyte in the light conduit 667 and exits the seal assembly 660 through the optical exit fiber 669. In some embodiments, the first seal 661, the second seal 664 and the third seal 665 of the seal assembly 660 may be independently manipulated in Cartesian x, y, z and rotational space to make and break fluidic connections. In other embodiments, the seals 661, 664 and 665 may be fixed in relation to the first sealing member 117 of the fluidic processor 100.

Figure 8:
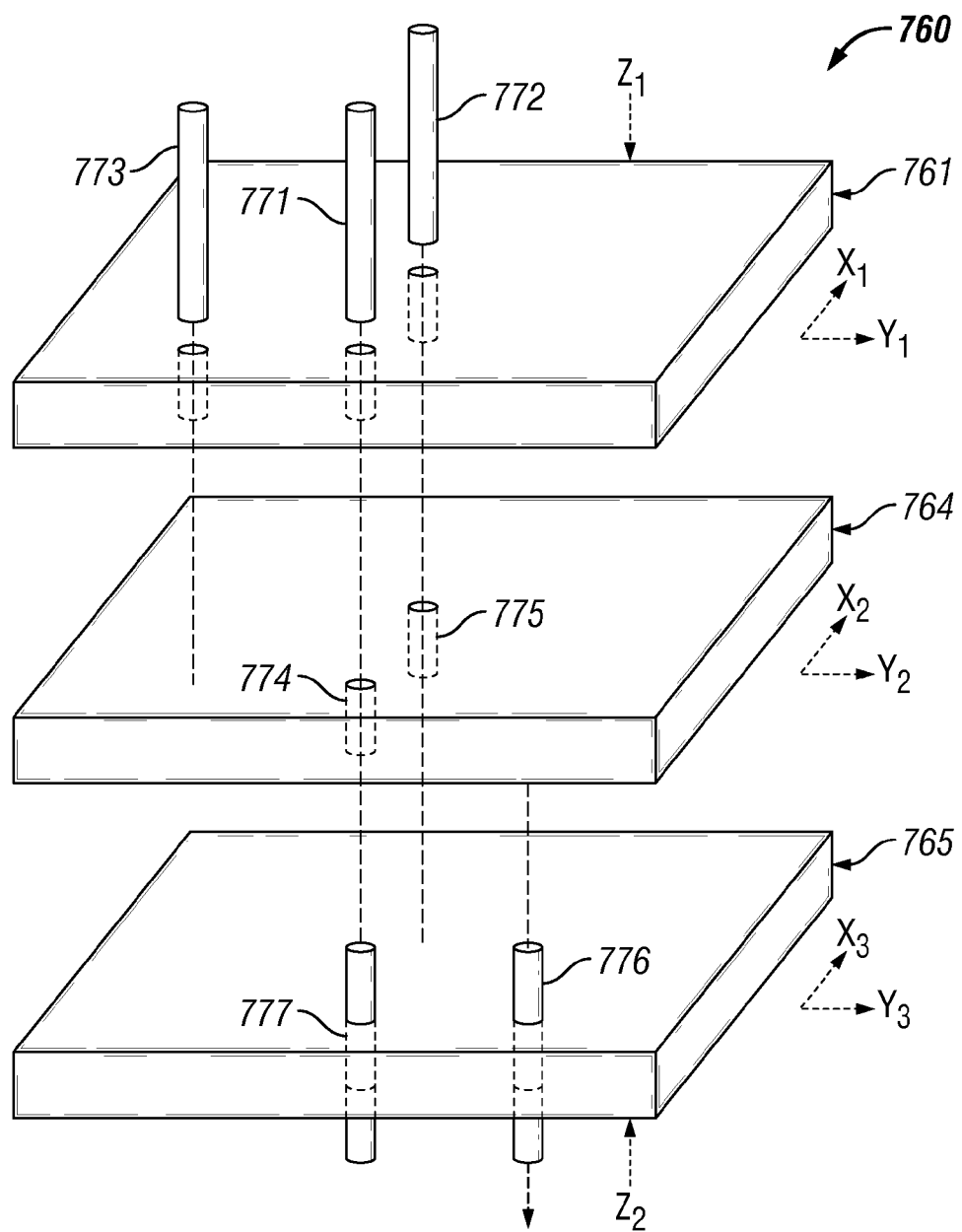
FIG. 8 is an exploded perspective view of an alternative exemplary seal assembly.

Referring next to FIG. 8 of the drawings, a perspective view of an alternative seal assembly which is suitable for implementation of an illustrative embodiment of the fluidic processor 100 is generally indicated by reference numeral 760. At least two detectors 771, 772, respectively, may be incorporated into the first seal 761. A fluid inlet conduit 773 may be moved into fluid communication with an optical conduit 774 or 775 in the second seal 764 and exit through a fluid exit conduit 776 in the third seal 765. The radiant energy may exit through an optical conduit 777 in the third seal 765.

Figure 9:
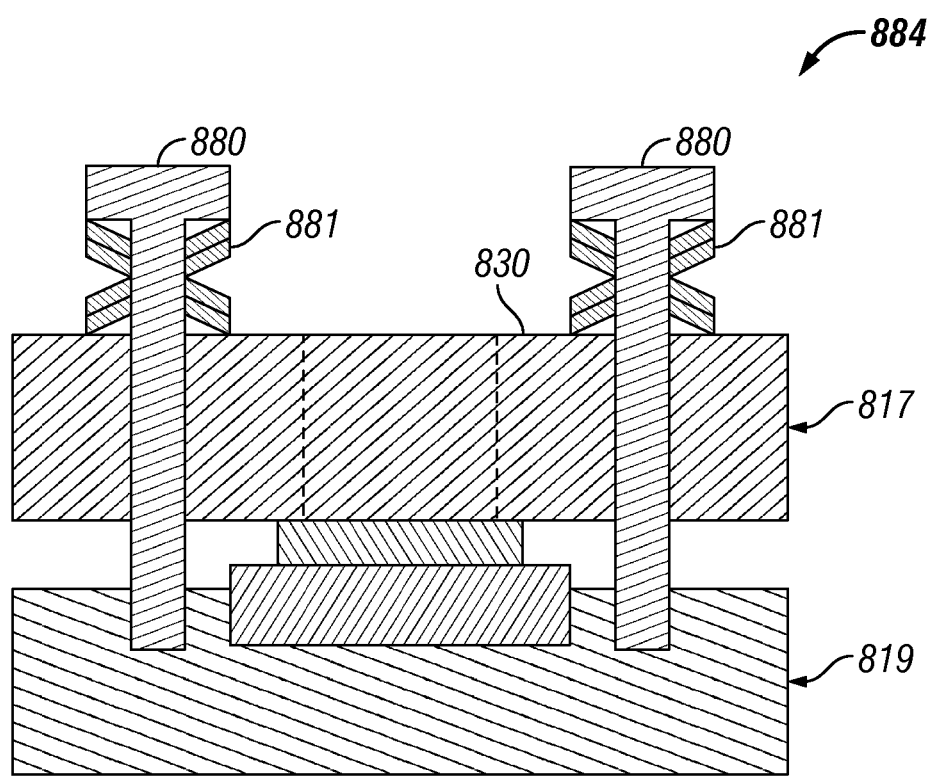
FIG. 9 is a cross-sectional view of an exemplary sealing mechanism which is suitable for implementation of an illustrative embodiment of the fluidic processor.

Referring next to FIG. 9 of the drawings, an exemplary sealing mechanism 884 which is suitable for implementation of the fluidic processor 100 is illustrated. The sealing mechanism 884 may include bolts 880 which extend through registering bolt openings (not illustrated) in the first sealing member 817 and the second sealing member 819. Belleville washers 881 may be provided between each bolt 880 and the first compression face 830 of the first sealing member 817. Accordingly, the bolts 880 and the belleville washers 881 apply compressive z axis force to the first sealing member 817 and the second sealing member 819 to maintain a seal between the first sealing member 817 and the second sealing member 819.

It will be appreciated by those skilled in the art that the fluidic processor 100 can be programmed to facilitate a large variety of fluidic operations. Alternatively, the fluidic processor 100 can be configured for more routine, repeat fluidic operations. In sharp contrast, conventional devices and associated fluidic conduits are made for a single or limited set of repetitive operations. FIG. 10 shows various methods that can be programmed into the fluidic processor 100 for operation in various applications.

Figure 10A:
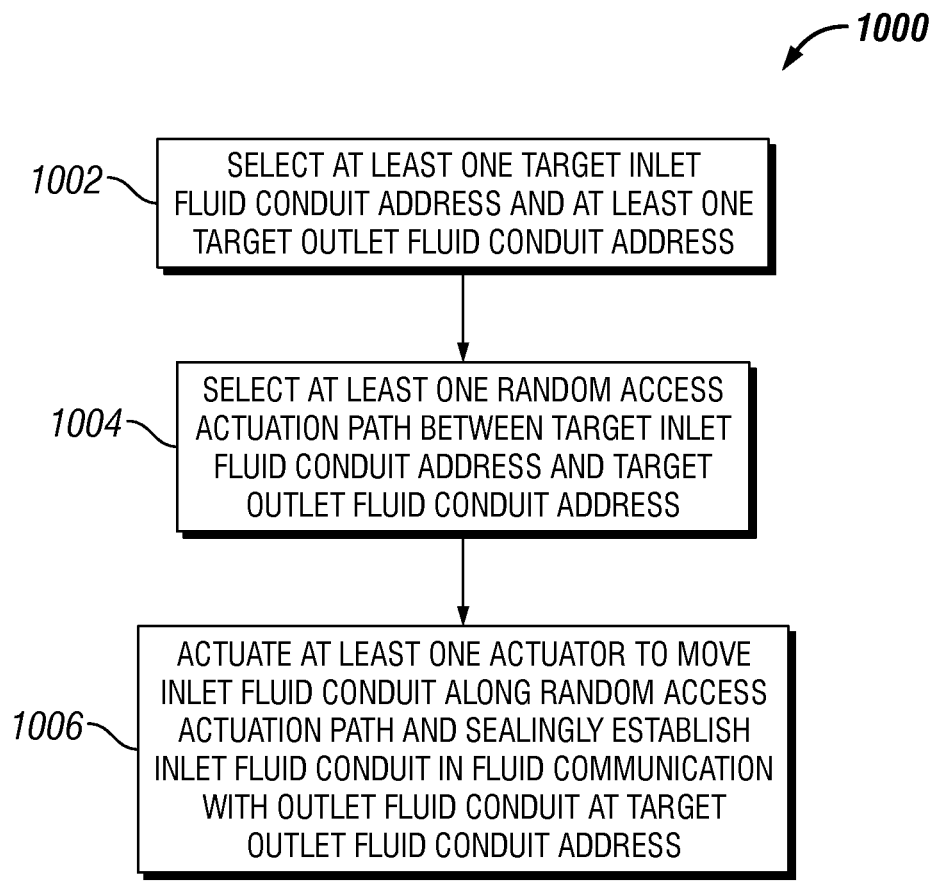
FIG. 10A is a flow diagram which summarizes an illustrative method of a method of operating a random access actuated fluid processor.

Referring next to FIG. 10A, a flow diagram 1000 which illustrates a method of operating a random access actuated fluid processor is illustrated. In block 1002, at least one target inlet fluid conduit address and at least one target outlet fluid conduit address may be selected. In block 1004, at least one random access actuation path between the target inlet fluid conduit address and the target outlet fluid conduit address may be selected. In block 1006, at least one actuator may be actuated to move an inlet fluid conduit along the random access actuation path and sealingly establish the inlet fluid conduit in fluid communication with the outlet fluid conduit at the target outlet fluid conduit address. In subsequent steps, fluid aliquots may be distributed through the plurality of inlet fluid conduits and delivered to an external analyzer through the plurality of outlet fluid conduits.

A potential application of the fluidic processor 100 is in low pressure sample preparation fluidics as is found in conventional clinical or molecular diagnostics fluidics systems. These systems may embody highly complex fluidics partially because carryover can never be acceptable. The present disclosure provides for both a fresh fluidic seal and a dynamic seal with each operation. In operation of the seal feed device 554 in FIG. 6, the sealing member 517 may be ejected after each fluidic operation to provide a clean fluidic conduit which is free of fluidic carry-over.

Another potential application of the fluidic processor 100 is in two-dimensional high-pressure liquid chromatography. A key advantage of the fluidic processor 100 for two-dimensional liquid chromatography is the capability to park aliquots from the eluting peak from the chromatography column in an array of fluidic conduits. Moreover, the fluidic processor 100 can be operated with no cross talk or sample carry over. In addition, the fluidic sealing members 117, 119 can be designed to minimize switching time through random access.

The fluidic processor 100 may be used to process all types of fluids including but not limited to gases. However, the materials which are necessary to create gas seals may differ greatly from the materials which are necessary to create liquid seals. Typically, gas seals employ graphite ferrules and stainless steel seats. In some embodiments, the fluidic processor 100 may utilize a combination of adhesives and graphic compression to accomplish gas sealing in the sealing members 117, 119. Another option that can readily be employed are elastomeric seals, and o-rings. If a hole at the sealing interface uses a slip-fit connection with stainless tube pressed into the seal, an o-ring can be used around the stainless tube with an annular groove fabricated in the sealing surface. The o-ring seal would seal very effectively in some applications. This would also require less force to press the two sealing surfaces together as o-rings seal with much lower force than a lapped surface.

The fluidic processor 100 may be used to bring multiple external components online through random access programming and judicious placement of fluid conduits. Applicable detectors include any detector that may require a flow cell or require a small aliquot of fluid to measure a response. Examples include but are not limited to spectroscopic techniques such as ultraviolet, visible, raman, refractive index, infrared, scattering (nephleometry), chemiluminescence and fluorescence. Electrochemical techniques are also contemplated which include but are not limited to potentiometry, ion selective electrodes, current techniques, voltammetry, polarography. Gas techniques include conductivity, infrared, ion mobility spectrometry and the like. The sealing members may also integrate an array of electrospray nozzles for random access spray introduction to mass spectrometry. In this embodiment, electrically-conducting nozzles may be formed on one external face of a sealing member. An exterior sheath may be placed around the nozzle for the introduction of nitrogen to form an aerosol.

Figure 11:
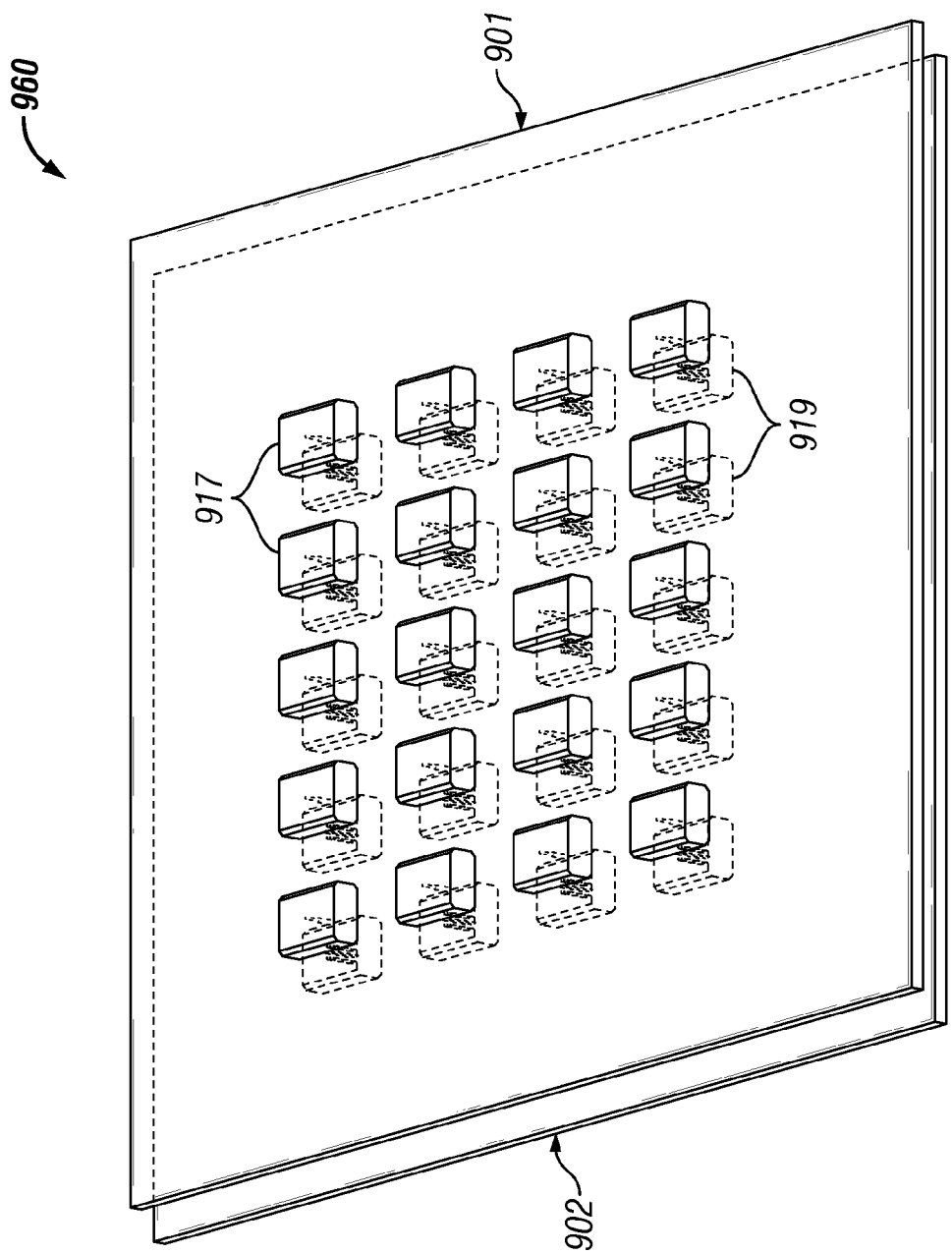
FIG. 11 is a perspective view of a seal assembly according to an alternative illustrative embodiment of the fluidic processor.

Referring next to FIG. 11 of the drawings, an alternative seal assembly 960 which is suitable for implementation of the fluidic processor 100 is shown. The seal assembly 960 may include an array of first sealing members 917 provided on the first housing 901 and an array of second sealing members 919 provided on the second housing 902. The second sealing members 917 may be adapted to sealingly engage the respective first sealing members 917 in operation of the fluidic processor 100 as was heretofore described. It will be appreciated by those skilled in the art that each of the first sealing members 917 and the second sealing members 919 may be individually replaced as deemed necessary. Moreover, more than one fluidic circuit can be driven by operation of the fluidic processor 100. Each first sealing member 917 and each second sealing member 919 may be individually loaded or unloaded when not in use.

Figure 12:
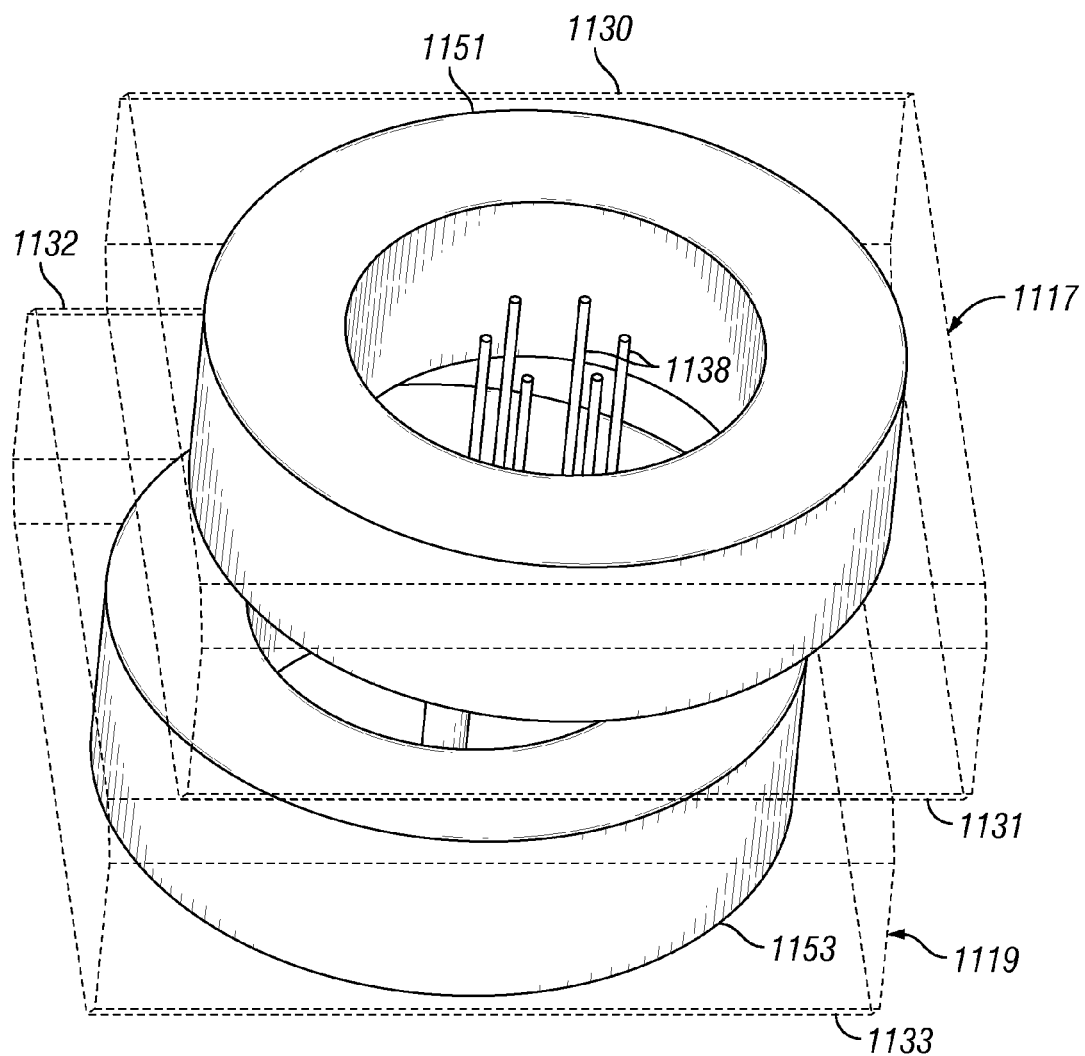
FIG. 12 is a perspective view illustrating a pair of sealing members and a sealing member magnet in each sealing member according to an alternative illustrative embodiment of the fluidic processor.

Referring next to FIG. 12 of the drawings, in some embodiments of the fluidic processor 100, at least one first sealing member magnet 1151 may be provided in the first sealing member 1117. At least one second sealing member magnet 1153 may be provided in the second sealing member 1119. Accordingly, in operation of the fluidic processor 100, which was heretofore described, the first sealing member magnet 1151 may magnetically engage the second sealing member magnet 1153 to impart Z-axis compression and form a fluid-tight seal between the first sealing face 1131 of the first sealing member 117 and the second sealing face 1132 of the second sealing member 1119.

While the preferred embodiments of the disclosure have been described above, it will be recognized and understood that various modifications can be made in the disclosure and the appended claims are intended to cover all such modifications which may fall within the spirit and scope of the disclosure.

The invention claimed is:

1. A fluidic processor, comprising:
   a first sealing member having a first sealing face, a first compressive face and at least one first sealing member fluid conduit;
   a second sealing member having a second sealing face, a second compressive face and at least one second sealing member fluid conduit;
   the second sealing face of the second sealing member being sealingly and slidingly engaged in a substantially fluid tight manner with the first sealing face of the first sealing member;
   a first linear actuator mechanically engaging the first sealing member, the first linear actuator substantially aligned with an X axis of a Cartesian coordinate system; and
   a second linear actuator mechanically engaging the second sealing member, the second linear actuator substantially aligned with a Y axis of the Cartesian coordinate system.

2. The fluidic processor of claim 1 further comprising at least one housing in fixed or sliding compressible engagement with at least one of the first sealing member and the second sealing member.

3. The fluidic processor of claim 1 further comprising a random access control system interfacing with the at least one actuator whereby make and break fluid communication is established between the at least one first sealing member fluid conduit and the at least one second sealing member fluid conduit by actuation of the at least one actuator in a substantially random manner.

4. The fluidic processor of claim 1 each of the first sealing member and the second sealing member is fabricated from a material selected from the group consisting of PPS, vespel, PEEK, acrylic, ultem, quartz, graphite, stainless, titanium, PTFE, ceramics, sorbent materials, and composites thereof.

5. The fluidic processor of claim 4 wherein each of the first sealing member and the second sealing member further comprises composites of the material or composites of the material filled with lubricious fillers.

6. The fluidic processor of claim 5 further comprising at least one internal fluid conduit disposed in fluid communication with the at least one second sealing member fluid conduit of the second sealing member.

7. The fluidic processor of claim 1 further comprising at least one hard lubricious coating on the first sealing member and the second sealing member.

8. The fluidic processor of claim 1 further comprising at least one inlet tube disposed in fluid communication with the at least one first sealing member fluid conduit of the first sealing member.

9. The fluidic processor of claim 1 further comprising a compressive force mechanism biasing the second sealing member against the first sealing member.

10. The fluidic processor of claim 9 wherein the compressive force mechanism comprises a belleville washer stack.

11. The fluidic processor of claim 10 further comprising at least one pressure disk between the belleville washer stack and the second sealing member.

12. The fluidic processor of claim 1 further comprising a Z-axis actuator mechanically engaging the second sealing member.

13. A fluidic processor, comprising:
a first housing having a first channel;
a first sealing member slidably disposed in the first channel and having a first sealing face, a first compressive face engaged by the first housing and at least one first sealing member fluid conduit;
a first linear actuator mechanically engaging the first sealing member, the first linear actuator substantially aligned with an X axis of a Cartesian coordinate system;
a second housing having a second channel oriented transverse to the first channel;
a second sealing member slidably disposed in the second channel and having a second sealing face, a second compressive face engaged by the second housing and at least one second sealing member fluid conduit;
the second sealing face of the second sealing member being sealingly and slidingly engaged in a substantially fluid tight manner with the first sealing face of the first sealing member;
a second linear actuator mechanically engaging the second sealing member, the second linear actuator substantially aligned with a Y axis of the Cartesian coordinate system.

14. The fluidic processor of claim 13 further comprising a random access control system interfacing with the at least one actuator whereby make and break fluid communication is established between the at least one first sealing member fluid conduit and the at least one second sealing member fluid conduit by actuation of the at least one actuator in a substantially random manner.

15. The fluidic processor of claim 13 further comprising a compressive force mechanism including a belleville washer stack and at least one pressure disk engaged by the belleville washer stack and biasing the second sealing member against the first sealing member.

16. The fluidic processor of claim 13 further comprising a Z-axis actuator mechanically engaging the second sealing member.

17. A fluidic processor, comprising:
a first housing having a first channel;
a first sealing member slidably disposed in the first channel and having a first sealing face, a first compressive face engaged by the first housing and at least one first sealing member fluid conduit;
a first actuator mechanically engaging the first sealing member;
a second housing having a second channel oriented transverse to the first channel;
a second sealing member slidably disposed in the second channel and having a second sealing face, a second compressive face engaged by the second housing and at least one second sealing member fluid conduit;
the second sealing face of the second sealing member being sealingly and slidingly engaged in a substantially fluid tight manner with the first sealing face of the first sealing member;
a seal assembly having a first seal engaged by the first sealing member, a second seal engaged by the first seal, a third seal engaged by the second seal and engaging the second sealing member, at least one fluid inlet conduit in the first seal and communicating with the at least one first sealing member fluid conduit of the first sealing member, at least one surface conduit in the second seal and communicating with the at least one fluid inlet conduit of the first seal and a fluid exit conduit in the third seal and communicating with the at least one surface conduit of the second seal and the at least one second sealing member fluid conduit of the second sealing member; and
a second actuator mechanically engaging the second sealing member.

18. The fluidic processor of claim 17 further comprising an optical fiber in the first seal and an optical exit fiber in the third seal.

19. The fluidic processor of claim 17 further comprising a compressive force mechanism including a belleville washer stack and at least one pressure disk engaged by the belleville washer stack and biasing the second sealing member against the first sealing member.

20. The fluidic processor of claim 17 further comprising a Z-axis actuator mechanically engaging the second sealing member.

* * * * *